(12) United States Patent
Shoenfeld

(10) Patent No.: US 12,239,612 B2
(45) Date of Patent: Mar. 4, 2025

(54) MEDICATION DISPENSING ARRANGEMENT WITHOUT SCANNING

(71) Applicant: Norman A. Shoenfeld, Cypress, TX (US)

(72) Inventor: Norman A. Shoenfeld, Cypress, TX (US)

(73) Assignee: S&SX-ray Products, Inc., Houston, TX (US)

( * ) Notice: Subject to any disclaimer, the term of this patent is extended or adjusted under 35 U.S.C. 154(b) by 0 days.

(21) Appl. No.: 18/231,836

(22) Filed: Aug. 9, 2023

(65) Prior Publication Data
US 2023/0398038 A1 Dec. 14, 2023

Related U.S. Application Data

(62) Division of application No. 17/064,760, filed on Oct. 7, 2020, now Pat. No. 11,759,397.

(51) Int. Cl.
*A61J 7/00* (2006.01)
*G06Q 10/087* (2023.01)
*G16H 20/13* (2018.01)

(52) U.S. Cl.
CPC ............ *A61J 7/0069* (2013.01); *G16H 20/13* (2018.01); *A61J 2200/70* (2013.01); *A61J 2205/60* (2013.01); *G06Q 10/087* (2013.01)

(58) Field of Classification Search
CPC .... A61J 7/00; A61J 7/0069; A61J 7/70; A61J 2200/70; A61J 2205/60; G16H 20/13; G06Q 10/087
See application file for complete search history.

(56) References Cited

U.S. PATENT DOCUMENTS

| 7,369,919 | B2 * | 5/2008 | Vonk | G16H 20/10 700/242 |
| 7,922,037 | B2 * | 4/2011 | Ohmura | G06V 20/66 221/3 |
| 8,878,654 | B2 * | 11/2014 | Cohen-Alloro | G16H 20/13 340/572.1 |
| 9,477,816 | B2 * | 10/2016 | Dent | G16H 20/10 |
| 9,757,305 | B2 * | 9/2017 | Ika | A61J 7/0069 |
| 9,798,862 | B2 * | 10/2017 | Parviainen | A61J 7/0092 |
| 10,621,306 | B2 * | 4/2020 | Dent | G16H 20/13 |
| 11,311,460 | B1 * | 4/2022 | Gershoni | A61J 1/035 |
| 2005/0240305 | A1 * | 10/2005 | Bogash | G16H 20/13 700/242 |
| 2009/0152291 | A1 * | 6/2009 | Ohmura | G07F 17/0092 221/197 |
| 2011/0045114 | A1 * | 2/2011 | Whetstone, Jr. | A23G 1/21 264/219 |
| 2012/0154120 | A1 * | 6/2012 | Alloro | G16H 20/13 206/528 |

(Continued)

*Primary Examiner* — Michael Collins
(74) *Attorney, Agent, or Firm* — Bernhard P Molldrem, Jr.

(57) ABSTRACT

A pharmacy tray for medications and medical items for patient treatment kit is placed onto a shelf that carries a grid of optical presence sensors. The location and identification of each item in the tray is recorded on a digital inventory for that tray. At the patient treatment site each item taken is recorded and the remaining inventory is updated without scanning the items. Each pharmacy tray bears a unique identifier that can be read at the patient treatment site to obtain the kit inventory for that tray.

16 Claims, 8 Drawing Sheets

(56) References Cited

U.S. PATENT DOCUMENTS

| | | | |
|---|---|---|---|
| 2013/0218330 A1* | 8/2013 | Chudy | G07F 17/0092 |
| | | | 700/244 |
| 2014/0261883 A1* | 9/2014 | Dent | G16H 20/13 |
| | | | 141/192 |
| 2018/0107976 A1* | 4/2018 | Sambrailo | G06Q 10/0833 |
| 2019/0127102 A1* | 5/2019 | Chudy | B65B 7/2871 |

* cited by examiner

```
┌─────────────────────────────────────────────────────┐
│                              PHARMATRAY             │
│  ┌──────────────────┐                               │
│  │ ENTER MEDICATIONS│        SCAN TRAY ID:          │
│  │  INTO DATABASE   │                    ─52        │
│  └──────────────────┘        ┌─────────┐  ┌──────┐  │
│                              │  54320  │  │REMOVE│  │
│                              └─────────┘  │ TRAY │  │
│        PHARM ONLY-MED SCAN                └──────┘  │
│                              ┌─────────┐            │
│                              │    1    │            │
│                              └─────────┘            │
│      ⎧ MEDICATION: AMIODALARONE 150mg               │
│   54 ⎨ LOT #884AF4539                               │
│      ⎨ EXP. DATE: 03/17/2022                    50  │
│      ⎩ added to tray: 54320 row2 item6              │
│                                                     │
└─────────────────────────────────────────────────────┘
```

FIG.8

```
┌─────────────────────────────────────────────────────┐
│              Scan New Tray ┌──────┐  ┌──────┐       │
│                            └──────┘  │INSERT│       │
│                                      └──────┘   56  │
│                                                     │
│  Enter/Scan Drug ID:  ┌──────────────────────┐      │
│                       └──────────────────────┘      │
│  Enter Drug Description ┌────────────────────┐      │
│                         └────────────────────┘      │
│  Enter Lot #          ┌──────────────────────┐      │
│                       └──────────────────────┘      │
│  Enter Exp. Date      ┌──────────────────────┐      │
│  (mm/dd/yyyy)         └──────────────────────┘      │
│  Controlled Drug (y/n?  on  oy                      │
│                                                     │
│                            ┌──────┐  ┌─────┐        │
│                            │RETURN│  │ENTER│        │
│                            └──────┘  └─────┘        │
└─────────────────────────────────────────────────────┘
```

FIG.9

| | | | | | | |
|---|---|---|---|---|---|---|
| 1 | | | | | | |
| 2 | 5 | 0719 | ABC123444 | LIDOCANE 1% 10 ml | A32455 | N | 12/12/2025 |
| 3 | 6 | 1036 | AAA1111538 | LIDOCANE 2% 10 ml | G645890 | N | 12/23/2024 |
| 4 | 5 | 443 | BBB2222 | EPINEPHRINE 1:10000 3ml | F545888 | N | 12/3/2021 |
| 5 | 8 | 917 | CCC44444444 | AMLODIPINE 10 ml | D3324444 | N | 07/22/2025 |
| 6 | 9 | 616 | DDD55555555 | LISINOPRIL 10mg tablet | R449077 | N | 04/02/2026 |
| 7 | 10 | 715 | DDD5555454555 | ADDERALL 30mg ER capsule | H5633419 | Y | 11/18/2021 |
| 8 | 11 | 315 | EEE6666666 | MORPHINE 2mg IV | LK99603 | Y | 12/12/2020 |
| 9 | 12 | 496 | 11111111 | ASA 5gr | YY9855543 | N | 06/07/2024 |
| 10 | 13 | 922 | 22222222 | LABETALOL 20mg inj | 6569066 | N | 06/08/2025 |
| 11 | 14 | 109 | 33333333 | AMIODARONE 150mg inj | 884AF4539 | N | 12/03/2022 |
| 12 | 15 | 551 | 44444444 | PHENTOLAMINE 5mg inj | GH3612589 | N | 04/25/2024 |
| 13 | 16 | 790 | 55555555 | PREDNISONE 10mg tablet | T08966270 | N | 06/21/2022 |
| | 17 | 433 | 66666666 | DECADRON 6mg inj | CV3287509 | N | 11/07/2022 |

MEDICATION DISPENSING ARRANGEMENT WITHOUT SCANNING

This is a Divisional Application of my copending application, Ser. No. 17/064,760, filed Oct. 7, 2020, now U.S. Pat. No. 11,759,397, granted Sep. 19, 2023.

BACKGROUND OF THE INVENTION

This invention relates to devices and equipment for dispensing medications and related items, and for automatically tracking an inventory of the contents of a medications tray or kit without requiring scanning the dispensed items at a patient treatment site.

The invention is more particularly concerned with a pharmacy tray or flat carrier in which medications and medical items are retained in particular open compartments or bins in the tray or carrier with open or uncovered tops but with a closed off bottom wall, and where the medications and medical items can be loaded according to a pharmacy kit plan or predetermined inventory, and later dispensed by a medical practitioner at a patient treatment site. The patient treatment site may be a surgical operating room, an emergency care facility, a cardiac care facility, a patient room or a clinic, for example. One useful place for a pharmaceutical kit tray is in an emergency room crash cart, where a supply of medications must be kept available for use on an immediate basis. Another example is an anesthesia cart for use in an operating room during patient surgery. This type of pre-filled pharmaceutical tray can also be used in a pass-through cabinet or in an automated dispensing cabinet. The tray is configured for loading the compartments by placing the medical items directly into the respective compartments through the open top, and accessing the needed medical items by reaching in and withdrawing the medical item through the open top. The tray has a geometry to ensure that the tray fits one way and only one way into the supporting shelf when it is loaded at pharmacy and when it is being accessed at the surgery or other treatment location.

One attempt to automate the inventory control for a medications kit tray has been proposed, employing radio-frequency identification tags (RFID tags). These RFID tags are to be attached to each item in a medications kit for a given tray when the tray is loaded at a hospital pharmacy. Each unique RFID code is associated with a particular medication or other item when the medication item is selected for the kit. At that same time the pharmacy technician has to enter an identification of the item and other information such as an expiration date. This may require entry by hand, or can be acquired by scanning a bar code.

When the medication items are dispensed at the patient treatment site, each selected item can be scanned with an RFID reader. The contents of an entire kit or tray may be checked by placing the tray into an enclosure and then scanning all the RFID tags of all the items in the kit to identify which ones are present and which ones are missing (by comparison with a kit plan or predetermined inventory schedule). An arrangement using RFID tags in this manner is described in McDonald et al Publication No. US 2013/0035950.

This system just described has a few drawbacks. The filling or loading process requires the pharmacist or pharmacy technician to keep a supply of RFID tags on hand and apply one onto each item when loaded into the pharmacy kit, and to scan each RFID tag as well as capture other required information such as the identity of the item and its expiration date. At the patient treatment site, each item that is dispensed may be scanned, although this is not automatically carried out, if it is performed. Also an RFID scanning kit box must be present at least at the hospital pharmacy to capture the inventory of the entire kit tray both upon filling and when returned to pharmacy from the treatment site. These boxes can be quite large and require significant space at the loading site.

Moreover, the RFID-based system does not provide a real-time update of the remaining inventory for any given medications tray when the kit tray is in use, and thus not automatically presented to the dispensing physician or to the pharmacy department.

Thus, a need remains for a system in which the required medications, syringes, ampules, and other items stored in a medications tray or bin can be easily accessed and administered without having to scan the items when doing so, and which will also update the inventory, i.e., the list of the contents of the tray, automatically upon accessing the items in the tray.

OBJECTS AND SUMMARY OF THE INVENTION

Accordingly, it is an object of the present invention to provide one or more trays pre-stocked or filled with a predetermined kit or set of medications for a given task, and which avoids the drawbacks mentioned above that inhabit the prior art.

It is a more specific object to provide a medications system with automated control of inventory of each such tray, without scanning, when items are removed from the tray.

It is another object to provide a system of loading each such tray without having to attach an additional part, such as an RFID tag, to each medication.

It is a further object to provide a system of trays and one or more shelves on which the trays are placed, in which an inventory of each tray is provided in digital form when the tray is accessed and where the inventory is automatically updated, and refreshed when each item in the tray is removed for dispensing.

According to an aspect of the present invention, a medication dispensing arrangement is provided for dispensing medications at a patient treatment site, for example in a crash cart employed for emergency medicine. This system automatically records the removal of each medication or item from the tray or kit for and automatically updates inventory of the medications and medical items in real time when any of the medications or medical items is removed from the medical dispensing arrangement at the patient treatment site.

A preferred embodiment has at least one medications tray, which has a floor that is transparent, at least in part, and has dividing walls forming a plurality of compartments, without lids or top covers, in the tray in a predetermined pattern or matrix to accommodate the medications and other items that may be needed. The compartments are configured to accept and hold a particular medication or medical item e.g., a syringe or a phial of an injectable or topically applied medication. The tray is also configured so that the floor has a respective transparent window at the location of each compartment in the tray. The compartments, being open at the top, permit immediate physician access to the medication or syringe. The cart or cabinet has at least one shelf on which the tray is placed for use in the patient treatment area. Each shelf has a plurality of optical presence sensors, with one or more sensors being positioned at the respective locations of the windows when the tray is positioned on the shelf. Associated data processing electronics are incorporated into the system, having inputs coupled to the optical presence sensors, and a memory storing an inventory of each tray including each tray's unique identifying data and the identity of each of the medications and medical articles loaded into and is stored in the tray's respective compartments. As above, the inventory data may be stored locally, but is also stored remotely from the cart on a server, either in the hospital, the pharmacy, or "in the cloud." The term "optical presence sensor" as used herein is not limited to the visible and infrared spectra, but could include other spectra of electromagnetic radiation. In some implementations, the shelf maybe a plate with an array of sensors of uniform density, e.g., a regular array of twelve-by-sixteen, in which there many be one or more than one sensor aligned with each given compartment on the associated tray. The shelf may have different densities of sensors in different regions. Locations of compartments for small items would need a higher density of sensors. Those areas corresponding to locations of large compartments would have a lesser density of sensors. Also, the tray may have a completely transparent (or transparent to infrared) bottom or floor.

The trays and shelves are constructed with respective complementary alignment structure to ensure that the at least one shelf can be positioned at only one position and in only one orientation on the shelf. This can be implemented with tabs extending down from the tray to fit into recesses in the shelf, and with the tabs and recesses asymmetrically positioned so that the tray fits the shelf in only one way. This may be done with the tabs protruding upward from the plate or shelf to fit into molded recesses in on the overlying tray, which has the advantage of creating a flat-bottom tray which may be easier to transport.

The floor of the tray may be entirely transparent to the wavelengths needed for the presence detectors, or the floor can be formed of transparent material in selected places to correspond to positions of the sensors on the associated shelf. The presence sensors can be available optical presence sensors, favorably to include surface-mount IR presence sensors.

The respective trays are individually marked with unique identifiers, and favorably are labeled with an optical coded symbol containing data uniquely identifying each such tray.

The invention is also directed to a process or method of dispensing medications and medical items from a medications cart or cabinet at a patient treatment site, especially for example in an emergency environment in which the selection and administration of the medication must be performed quickly, but where the item used must be accurately identified, such as in the use of a crash cart in treating a patient experiencing cardiac arrest.

In this process, the medications and medical items taken are identified automatically without scanning when selected and removed when time is critical, and the inventory of the contents of the medication cart of cabinet is automatically updated each time a medication or medical item is taken.

The medications tray of the type described above is placed onto a shelf at a loading station, typically located at the pharmacy department of the hospital or other care center. As aforesaid, the tray has a floor and dividing walls so as to form a plurality of individual compartments. The tray's compartments lie in a predetermined pattern so as to align with corresponding presence detectors in the shelf at the loading station. The tray's compartments are each configured to accept and hold a particular medication or medical item. The floor of the tray has respective transparent windows therein at locations of the respective compartments. Also the tray bears a unique identifying code, which may for example be a 2-D bar coded symbol. As aforesaid also, the shelf includes a number of optical presence sensors, and these are positioned at the respective locations of the windows in the floor of the tray when such a tray is positioned on the shelf.

At the commencement of the filling of the medications kit for the tray, the unique identifying code for the tray is scanned and recorded in memory. Then, one-by-one, the selected medications and medical items are loaded into their respective compartments in the tray. In this process, each time the medications or medical items are selected to be placed into respective compartments in the tray, the identity of the selected medication or medical item is picked up e.g. by scanning a bar code label on the item, or by manually keying information, and is entered into a digitally stored inventory for that tray. Then the medication or medical item is placed into a respective one of the compartments of the tray. At that point, the presence detector associated with that respective compartment produces a signal to associate the location of that compartment in the tray with such medication or medical item in the inventory. This associates the tray, the compartment, and the identity of the item itself plus other associated information such as expiration date. This is then repeated, i.e., selecting, scanning and placing, for the remaining medications and medical items to be placed into the tray, completing the medications kit. The digitally stored inventory for that kit, including the tray identification and the contents and item compartment locations, can be transmitted to the digital processing system associated with the cart or cabinet. This data can also be transmitted to the pharmacy central computer system. The tray for the pre-loaded medications kit is loaded onto a shelf at the crash cart or other medications cart or cabinet. That shelf includes a plurality of optical presence sensors positioned at respective locations of the tray's windows when the tray is positioned on such shelf. At the time of placing the tray on the shelf, the tray's unique identifying code is scanned and entered into the digital processing system for crash cart (or other cart or cabinet). This may result in the identity of the tray being displayed on a display device at the cart or cabinet, and favorably displaying on the monitor the identity of each medication or medical item in the tray. This process may be done solely in background without display of the information. As the medications or other items are taken from the tray for administration to a patient, the identity of the selected medication or medical item is also displayed.

Favorably, the operating circuitry includes a suitable data processing and data memory so that the configuration for a number of trays and the drug and medication items in those that are filled can be available and displayed on video monitor. The need for the data memory on the cart may be reduced by having the inventory data retrievable from the server or cloud service, and not on the cart itself. The cart would not serve as the sole repository of this data.

The autosensing of inventory in each tray, bin or drawer can be employed in any suitable environment in which the items from the tray or kit are to be administered to a patient, including a crash cart, as mentioned above, or a pass-through cabinet, anesthesia cart, or automated dispensing cabinet. The tray (which may be a bin or a drawer) is organized as a divider tray, where there is an individual space reserved for each medication, syringe, or other item. There are reflective IR sensors present for respective locations, automatically sensing when an item has been removed, and saving this value in memory. This stored data allows tracking of inventory directly, and in real time or near real time in pharmacy, and without the need for an anesthesiologist or nurse to scan each item when removed from the cabinet or cart.

To sum up the process, a pharmacy technician loads the tray, scanning the unique tray number, e.g., a bar code on the side of the tray. Then each item of inventory is scanned as it is placed into a grid location, i.e. compartment of the tray. This is carried out with the tray placed on a shelf, i.e., a bed where there are sensors positioned according to the same matrix, e.g., infrared sensors detecting the presence or absence of items in the tray. These sensors are at the same locations as the items in the tray, so the filled locations are known, and the location designation itself does not have to be scanned or keyed in manually. The location is identified by the sensor when it recognizes that something was place in its view. When the loading of the tray is complete, there is a digital table created in the system of what each item is that is present in that tray, and what its position is in the tray. The information in this table is then stored in a networked data base.

When the tray is placed into a cart or cabinet, e.g., a crash cart, the tray number is scanned as is the drawer identification of the cart or cabinet. Then, as items are removed from any given tray in the cart, a signal from the sensor grid is received in the associated data processor in the cart, as well as others networked with it, such as in the pharmacy department. Thus as the item or items are removed from the tray, the networked system identifies exactly which item was removed, without need for scanning the individual item, which can be a burden during an emergency or during surgery in the OR when taking medications from a cart or cabinet.

As an additional note, the sensor grid in the pharmacy loading facility and the sensor grid in the cart or cabinet both have a fixed grid configuration. The arrangement of the compartments on the trays may vary, depending on purpose, but are designed so they can be serviced by the same grid of sensors. The item's presence and the item's removal can be sensed and recorded using the same configuration grid.

Also, the trays themselves are most favorably of a shallow design, as they are intended to hold only a single item per compartment. This differs from many current styles of tray which have deep slots with the tray compartments holding two or more of some items. This shallow design then permits an increased density of stacked drawers, and helps achieve a quick visual identification of empty slots or compartments in the tray, and helps the medical practitioner know what was taken out and needs to be replaced.

These and other configurations, features, and advantages of this invention will become apparent from the ensuing description of preferred embodiment of this invention, with reference to the accompanying Drawing.

BRIEF DESCRIPTION OF THE DRAWING

FIG. 8 shows a screen appearing at the pharmacy loading station while medications and/or medical items are placed in the tray to fill a kit order.

FIG. 9 shows the screen displayed for each item as it is loaded into the tray.

FIG. 10 is a screen display of the kit inventory of contents of the tray, as stored in the system server memory.

DETAILED DESCRIPTION OF THE PREFERRED EMBODIMENTS

Figure 1:
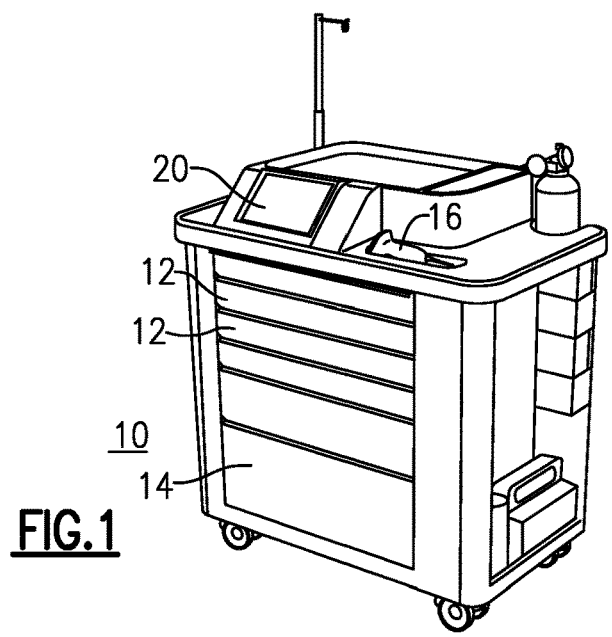
FIG. 1 is a front elevational view of medications cart for use in a hospital environment, here a crash cart for use in emergency medicine, in which the medications tray of this invention can be employed to advantage.

With reference to the Drawing, the medications tray of this invention may be used in any of several types of medical carts or cabinets, for example in an emergency medicine crash cart as shown here in FIG. 1. The crash cart 10 is a portable cabinet with casters or wheels, and can be pushed quickly into a patient treatment site in a hospital facility. Here the cart 10 has a number of pull-out drawers, including shallow drawers 12 for holding the emergency medications and which may contain a medications tray, with medications, dressings, syringes for quick and convenient access, and an associated platform or shelf, as will be described later. There are also one or two deeper drawers 14 for dressings, bandages, liquids such as Ringer's solution, and other large items. In this example, the cart 10 also can have a hospital computer with keyboard, and an associated video screen. Also shown here are a bar code scanner 16 and a monitor 20 for displaying patient vital information, cardiology activity, pulse rate and blood pressure, and other patient information.

Figure 2:
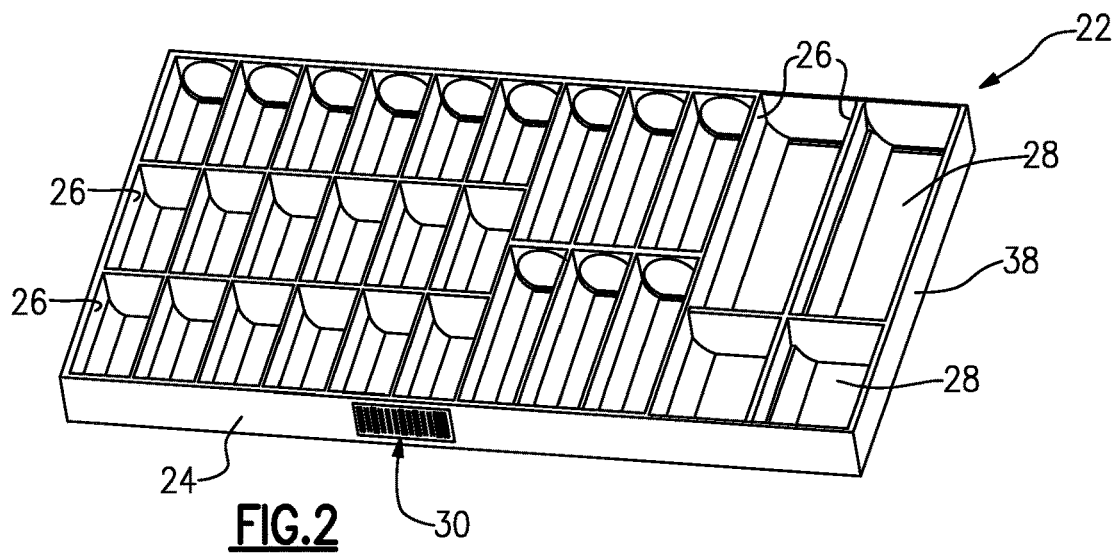
FIG. 2 is a perspective view from above of a medications tray according to an embodiment of this invention.
Figure 3:
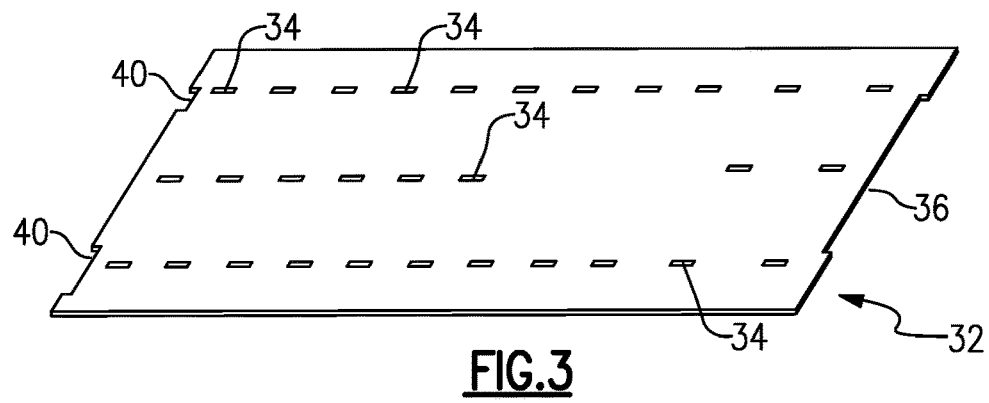
FIG. 3 is a perspective view from above of a shelf or loading/dispensing platform adapted to mate with the tray of FIG. 2.

The perspectives of FIGS. 2 and 3 show a tray 22 of the type that may be contained within any or each of the drawers 12, and an associated shelf or platform 32 on which the tray 22 is carried within the drawer 12. A similar shelf or platform would also be present in the hospital pharmacy where the trays are prepared and filled with the required medical items.

As shown in FIG. 2, the tray 22 is relatively shallow, designed to hold one item per compartment, and here having compartments arranged in a matrix to facilitate detection of which items are present and which are absent. The tray 22 in this embodiment is generally rectangular, with exterior walls 24, i.e., end and side walls, as well as internal divider walls 26 that rise from a floor 28. The floor is made either entirely of transparent plastic material or at least transparent at locations of the compartment locations as defined between the divider walls 26 or between divider wall and one or another of the exterior walls 26. One side wall 24 bears a bar coded symbol 30 that carries a numerical code to identify the specific one of the trays 22. This is scanned in when the tray 22 is filled at the pharmacy station and again when the filled tray is installed in the crash cart 10 or in another cart or cabinet.

FIG. 3 shows a shelf 32 or platform on which the tray 22 is held when it is filled at pharmacy and when it is placed into the appropriate drawer 12 in the cart 10. The shelf 32 is of the same geometry as the bottom or base of the tray 22, and there is corresponding structure on the tray and on the shelf to ensure that the tray fits in only one orientation on the shelf. On the surface of the shelf 32 there is a regular array or matrix of surface-mounted optical presence sensors 34, e.g., infrared sensitive, each being positioned to view through the transparent window 28 of a given compartment in the tray. Depending on the geometry of the matrix of the particular tray, some of the sensors 34 may be turned off and the remainder used, or all may be used.

The array of sensors 34 actually used (automatically determined by scanning in the identity of the tray 22) then corresponds to the matrix of compartments in the tray 22.

Figure 4:
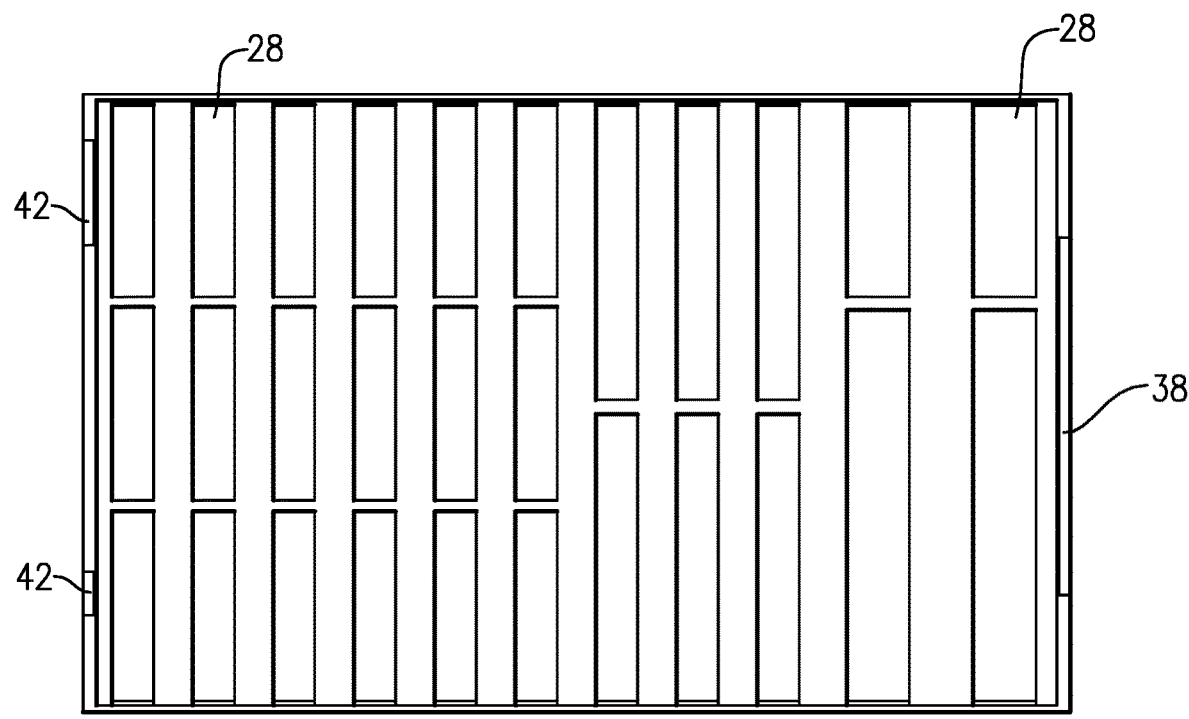
FIGS. 4 and 5 are a top plan view and a side elevation, respectively, of the tray according to one embodiment of this invention. cut away at line 4-4 of FIG. 3 showing the shade or cover in the full open position.
Figure 5:
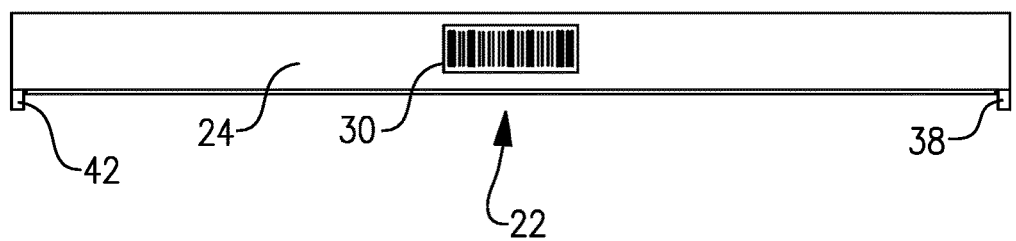

As shown in FIGS. 2 and 3, and also with reference to the bottom and side views of FIGS. 4 and 5, the tray 22 has tab a downward extending tab 38 (see also FIGS. 4 to 6) at one end that seats into a mating slot, notch or recess 36 in the corresponding end of the tray, and a pair of tabs 42, 42 at the opposite end of the tray 22 that mate with corresponding slots or gaps 40 in the shelf 32. These tabs (and corresponding slots or gaps) are asymmetrically arranged and are of different sizes so that the tray aligns with the shelf in only one possible orientation. This is evident in the bottom and side view of FIGS. 4 and 5. Note that the bottom wall or floor of the tray 22 can be of clear transparent plastic, either entirely or at least at the locations of the windows.

Figure 6:
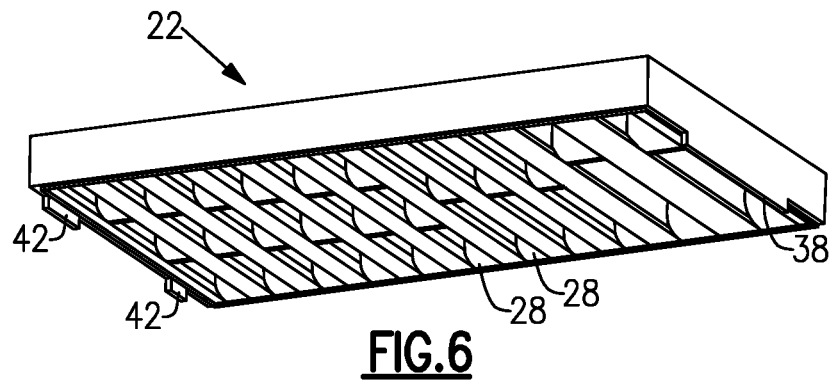
FIG. 6 is a perspective view from below showing transparent windows in the tray bottom and positioning tabs adapted to mate with recesses in the shelf or platform of FIG. 3
Figure 7:
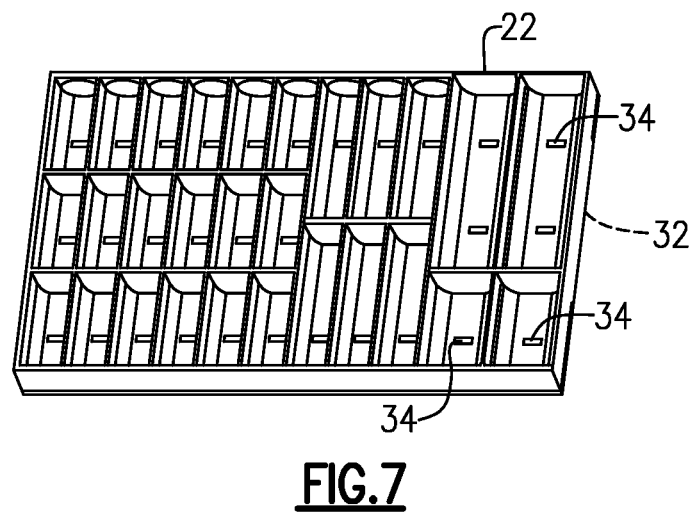
FIG. 7 is a perspective view showing the tray positioned on the shelf or loading/dispensing platform.

FIG. 6 is a perspective view featuring the underside of the tray showing the geometry of the tabs 38, 42 in this embodiment and illustrating the transparency of the windows 28. FIG. 7 illustrates the alignment of the tray 22 and shelf 32 such that the matrix of the surface-mounted sensors 34 aligns with the windows for the various compartments in the tray.

As aforesaid, the same type of shelf or platform is preferably used both at the pharmacy location where the tray is filled, and in the cart 10 at the patient treatment location, with the digital inventory of the tray being created upon loading the tray in pharmacy, and that being digitally sent to the crash cart 10 for identifying the medical items when removed from the tray.

FIG. 8 illustrates a typical screen 50 of the computer monitor at the pharmacy location. There, a new, empty tray has been placed on the pharmacy station for a pharmacy technician to fill the tray according to a prescribed plan or kit. First the technician scans the bar code 30 on the side of the tray, and the system automatically identifies the tray and places the tray identifier (here, "54320") in a tray ID box 52. The technician begins loading the medications and other items as listed in the kit into the appropriate compartments in the tray. For each element, the technician scans a bar code on the item, and then places the item into the tray, whereupon a presence detector 34 for that compartment logs the item in for that specific compartment. At that point the identity of the item appears at the position 54 on the screen. In this example, the item is a medication, Amiodarone, 150 mg injectable (syringe), with its lot number and expiration date (here, Aug. 17, 2022). The tray location in tray 54320 also appears at screen location 54, namely, row 2, item no. 6. This simple procedure is followed for each medication or other item for the particular kit that is being filled into the tray.

FIG. 9 is a screen 56 that appears when the technician need to manually enter the tray identifying number and/or the medication information when the medication is selected to place into the tray.

When filling of the tray 22 is complete, the inventory of the medications kit in the tray is stored in the server memory, as is the tray identity (here, tray no. 54320). This can appear on screen 60 (FIG. 10) as a chart listing the medication, lot number, whether it is controlled material, and its expiration date. The tray compartment location for each is also stored in memory, and this is transmitted to the computer on the cart 10 when the tray is installed there and its coded optical symbol is scanned in at the crash cart. Then, in the emergency room or other patient treatment site, as each medication is removed from the tray, the optical presence detector 34 associated with its location in the tray signals the cart computer 16 that this medication has been taken, and the tray's inventory record is automatically updated to reflect this. No further action is required on the part of the medical practitioner beyond picking the item up from the cart. No scanning of the item or manual data entry is required. The changes in the content of the tray are relayed automatically to the hospital pharmacy system, accompanied with patient information. As other items are removed from the tray 22, a signal from the grid of presence sensors 34 is received. Based on the recorded inventory of the tray, a record is kept of what items have been taken from the tray, and the time when each one has been taken, as well as a record of what items remain in the tray. All this information is developed without having to scan bar codes or RFID tags at the patient treatment site.

Figure 11:
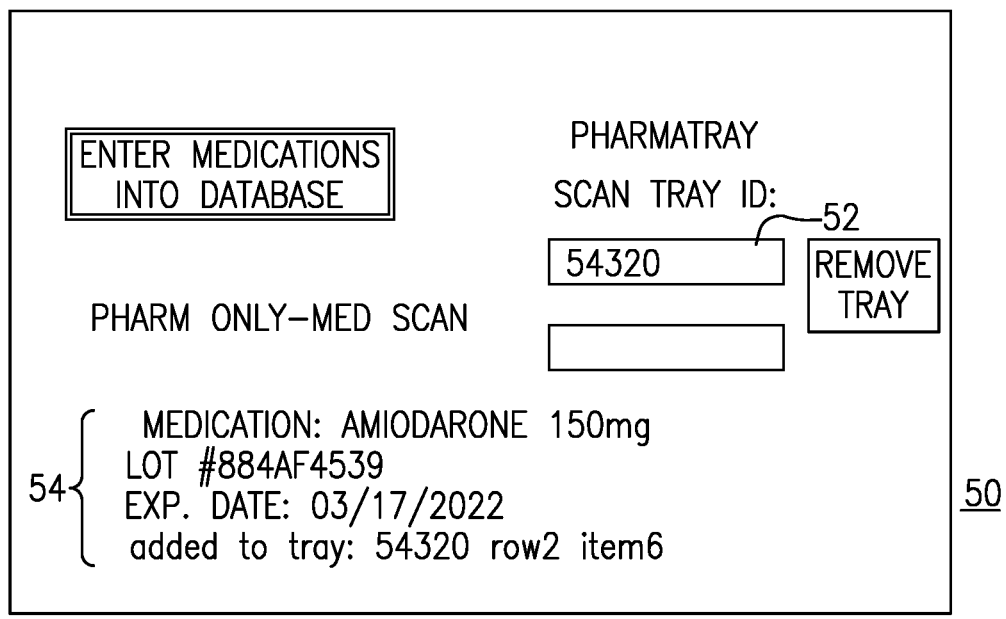
FIG. 11 shows a screen appearing on the medications cart at the place of administration to the patient.

FIG. 11 shows the screen at the crash cart 10 when the emergency medicine practitioner removes a medication from the tray 22 at the emergency room. This is similar to the loading screen (FIG. 8), displaying the same tray with ID 54320, as well as the medication, the medication lot number, expiration date, and tray location, all appearing at field 54 on the screen. This appears each time a medication is taken from the tray. Another screen (not shown) is available to the practitioner to display the tray contents including what items have been taken and which remain.

Figure 12:
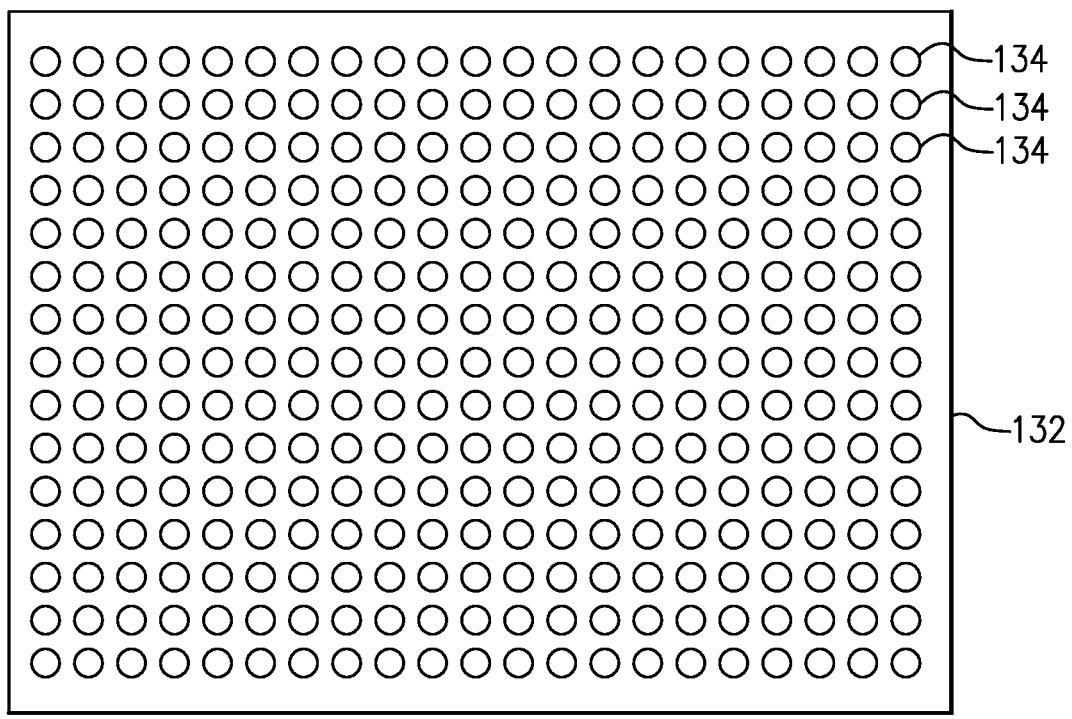
FIG. 12 is a perspective view of a possible shelf or loading/dispensing platform embodying this invention.

In this system as described, the sensor grid of the presence sensors 34 on the shelf or platform 32 is a fixed grid, and is employed with any of a multitude of trays. The compartment arrangement and configuration for each tray is known and kept in computer memory, and the individual sensors 34 in the grid are used or not used depending on the compartment configuration of the tray. Thus the trays can vary in their arrangement and use, but still be compatible with the same grid configuration of sensors 34. As shown in FIG. 12, the grid of sensors 134 on the shelf or platform 132 can be a grid of sensors evenly distributed on the platform 132. In this case, there is a rectangular grid of twenty-four columns by sixteen rows, although more or fewer sensors 134 can be present. In this case, different arrangements of tray divider walls can be used in the various trays, and the presence or absence of an object will be detected by one or more of the sensors where the items are stored, Different densities of sensors may then be needed with fewer sensors in areas where there are larger compartments. The software for the system would recognize for each tray, based on its identification read at the scan of the bar code symbol 30, and the software would then control which of the sensors 134 from the grid would be needed for that given tray, and which can be left off or ignored.

Figure 13:
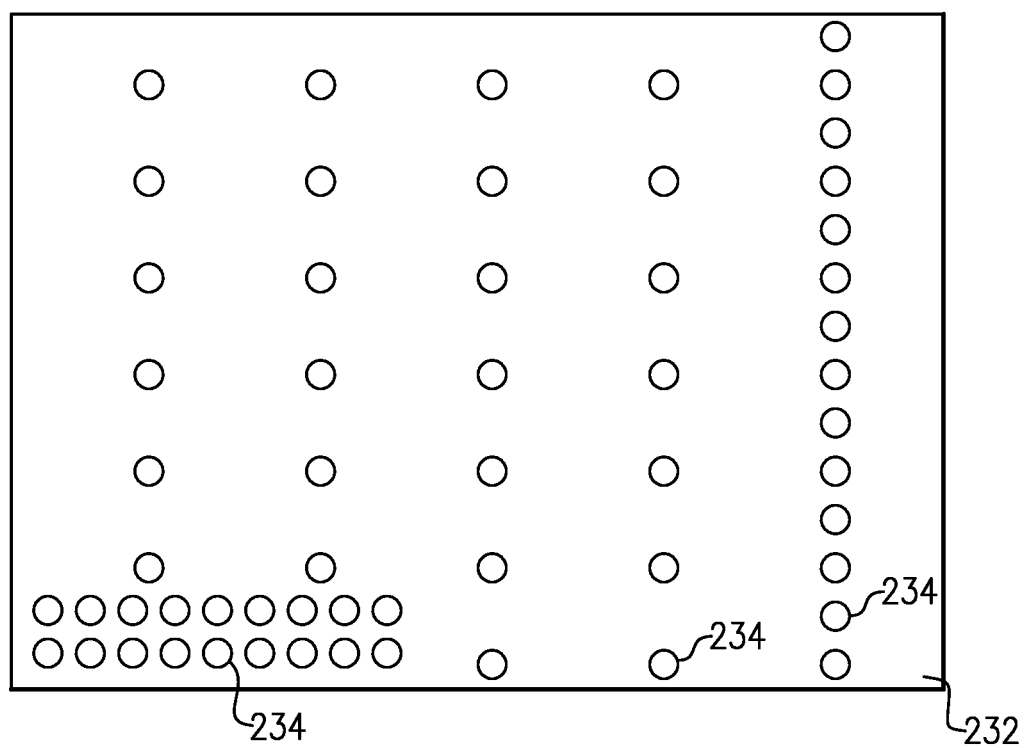
FIG. 13 is a perspective view of another possible shelf or loading/dispensing platform having different densities of sensors in different areas, also embodying this invention.

Another possible shelf or sensor plate 232 is shown in FIG. 13, there there are different densities of sensors 234 in different areas, to match locations of the compartments on a medications tray (not shown here). In this example, the compartments for small vials would go at the bottom left corner where there is a high density of sensors 134, and other areas where the sensors 234 are spaced further apart to correspond to compartments where larger medication items would be stored in the tray. Here there is another region where there is a higher density of sensors along the right side, where other smaller items might be stored.

While the invention has been described in terms of selected preferred embodiments, it should be understood that the invention is not limited only to those embodiments, but rather the scope of this invention is to be measured by the appended claims.

What is claimed is:

1. A method of dispensing medications and medical items from a medications cart or cabinet at a patient treatment site wherein the medications and medical items are identified automatically without scanning when selected and removed, and wherein an inventory of the contents of the medication cart of cabinet is automatically updated when the medication or medical item is taken, comprising placing a tray onto a shelf at a loading station, the tray having a floor and dividing walls forming a plurality of open-top compartments in said tray in a predetermined pattern; said compartments each being provided without a lid or cover and being configured to accept and hold a medication or medical item, said floor closing off each said compartment and having respective transparent windows therein at locations of said compartments and said tray having a unique identifying code thereon, and said shelf including a plurality of optical presence sensors positioned at respective locations of said windows when said at least one tray is positioned on said at least one shelf;

each said optical presence sensor detecting only the presence or absence of a medication or medical item in the respective one of said compartments;

recording a unique identifying code for said tray; and loading selected medications and medical items into said tray, including the steps of:

selecting medications and medical items to be placed into respective compartments in the tray, and for each said medication and medical item, entering an identity of the selected medication or medical item into a digitally stored inventory for said tray, and placing the medication or medical item into a respective one of said compartments of the tray, whereupon the presence detector associated with the respective compartment produces a signal to associate the location of said compartment in said tray with the identity of such medication or medical item in said inventory; and repeating the above-recited steps of selecting, entering, placing and associating for the remaining medications and medical items to be placed into said tray.

2. The method of dispensing medications and medical items according to claim 1, further comprising placing said tray, after the step of loading, into a medications cart or cabinet to be used at said patient dispensing location, and entering said unique identifying code for said tray into a digital processing system associated with said medications cart or cabinet.

3. The method of dispensing medications and medical items according to claim 2, further comprising transmitting said digitally stored inventory, including the identity of each medication and medical item and the location of the compartment in which it has been placed, to the digital processing system associated with said cart or cabinet.

4. The method of dispensing medications and medical items according to claim 1 further comprising placing said tray onto a shelf at said cart or cabinet, said shelf including a plurality of optical presence sensors positioned at respective locations of said windows when said at least one tray is positioned on said at least one shelf, and scanning said unique identifying code for said tray to enter said code into a digital processing system for said cart or cabinet.

5. The method of dispensing medications and medical items according to claim 4 further comprising displaying an identity of the tray on a display device at the cart or cabinet, and as each medication or medical item is selected and removed from the tray, displaying an identity of the selected medication or medical item.

6. The method of dispensing medications and medical items according to claim 5 further comprising automatically transmitting to a pharmacy location the digital inventory of the contents of said tray as each said medication or medical item is removed from said tray.

7. The method of dispensing medications and medical items according to claim 1, wherein said medication and medical and medical items are comprised of a predetermined mixed assortment of medications and medical items that form a medications kit, and said step of selecting includes selecting the medications and medical items of said medications kit and placing the same into respective compartments of said tray.

8. The method of dispensing medications and medical items according to claim 7, wherein said predetermined assortment includes at least one syringe of an injectable medication.

9. The method of dispensing medications and medical items according to claim 7, wherein said medications and medical items include at least one phial of a topically applied medication.

10. The method of dispensing medications and medical items according to claim 1, further comprising after the steps of selecting medications and medical items to be placed into respective compartments in the tray, and for each said medication and medical item, entering an identity of the selected medication or medical item into a digitally stored inventory for said tray, and placing the medication or medical item into a respective one of said compartments of the tray, whereupon the presence detector associated with the respective compartment produces a signal to associate the location of said compartment in said tray with such medication or medical item in said inventory; and repeating the above-recited steps of selecting, entering, and placing for remaining medications and medical items to be placed into said tray; automatically generating an inventory of the medications and medical items that are present in said tray, with each item being associated in said inventory with its respective compartment in said tray.

11. A tray for carrying medication and medical items, comprising a floor composed as a rectangular sheet of a material that is at least in part transparent;

a plurality of divider walls rising from said floor and dividing the tray into a plurality of compartments in a predetermined matrix pattern, said plurality of divider walls forming said compartments as open compartments without lid or cover, and said floor closing off each of said compartments;

said compartments being configured to accept and hold a medication or medical item;

said floor having respective transparent windows therein at locations of said compartments;

wherein the matrix pattern of said tray is asymmetric in front to rear and side to side dimensions; and wherein said tray has alignment projections thereon projecting vertically and of respective different geometry from one another at opposite ends of said tray, so as to fit in only one way into a dispensing shelf having a complementary matrix pattern.

12. The tray according to claim 11 wherein said floor is transparent only to infrared radiation at least at selected places in each of said compartments.

13. The tray according to claim 11, comprising a machine-readable unique identifying code placed on a wall of said tray.

14. The tray according to claim 13, wherein said tray is one of a plurality of kit trays, each of which bears a different said machine-readable unique identifying code.

15. The tray according to claim 11 wherein said compartments are of at least two different sizes to accommodate medications and medical items of different sizes.

16. The tray according to claim 11, wherein the matrix pattern of said tray is asymmetric in front to rear and side to side dimensions, so as to fit in only one way into a dispensing shelf having a complementary matrix pattern.

* * * * *